United States Patent
Houston et al.

(10) Patent No.: US 8,454,675 B2
(45) Date of Patent: Jun. 4, 2013

(54) INTERNAL FORMATION FOR A CONDUIT

(75) Inventors: John Graeme Houston, Perth (GB); Robert Gordon Hood, Perth & Kinross (GB); Peter Arno Stonebridge, Perth (GB); John Bruce Cameron Dick, Coupar Angus (GB)

(73) Assignee: Tayside Flow Technologies Ltd. (GB)

( * ) Notice: Subject to any disclaimer, the term of this patent is extended or adjusted under 35 U.S.C. 154(b) by 203 days.

(21) Appl. No.: 10/562,471

(22) PCT Filed: May 24, 2004

(86) PCT No.: PCT/GB2004/002216
§ 371 (c)(1),
(2), (4) Date: Nov. 13, 2006

(87) PCT Pub. No.: WO2005/004751
PCT Pub. Date: Jan. 20, 2005

(65) Prior Publication Data
US 2007/0106373 A1    May 10, 2007

(30) Foreign Application Priority Data
Jul. 4, 2003   (GB) .................................. 0315714.6

(51) Int. Cl.
*A61F 2/06* (2006.01)
(52) U.S. Cl.
USPC ........................................................ 623/1.15
(58) Field of Classification Search
USPC ...... 623/1.1–1.25, 1.27–1.33, 1.44, 1.5–1.54; 138/37, 39; 606/108, 192, 194
See application file for complete search history.

(56) References Cited

U.S. PATENT DOCUMENTS

| | | | |
|---|---|---|---|
| 3,197,853 A | 8/1965 | Waldt | |
| 4,604,762 A | 8/1986 | Robinson | |
| 4,629,458 A | 12/1986 | Pinchuk | |
| 5,108,417 A * | 4/1992 | Sawyer | 623/1.22 |
| 5,238,642 A | 8/1993 | Benquet et al. | |
| 5,344,425 A * | 9/1994 | Sawyer | 606/198 |
| 5,619,878 A | 4/1997 | Grosjean et al. | |
| 5,653,745 A | 8/1997 | Trescony et al. | |
| 5,756,035 A | 5/1998 | Underwood et al. | |
| 5,992,465 A * | 11/1999 | Jansen | 138/37 |
| 6,099,557 A * | 8/2000 | Schmitt | 623/1.1 |
| 6,173,763 B1 * | 1/2001 | Sano et al. | 165/133 |
| 6,190,404 B1 * | 2/2001 | Palmaz et al. | 623/1.15 |

(Continued)

FOREIGN PATENT DOCUMENTS

| | | |
|---|---|---|
| AT | 134543 | 8/1933 |
| EP | 1036551 A2 | 9/2000 |

(Continued)

OTHER PUBLICATIONS

Caro et al., "Mechanics of the Circulation", 2011, pp. 56-58, Publisher: Cambridge University Press, Published in: UK.

*Primary Examiner* — Victor Nguyen
*Assistant Examiner* — Jocelin Tanner
(74) *Attorney, Agent, or Firm* — Kaplan Breyer Schwarz & Ottesen, LLP

(57) ABSTRACT

An internal formation for a conduit. The formation has a longitudinally extending member adapted to extend along an inside surface of at least a portion of the length of the conduit. The longitudinally extending member has an asymmetric profile in a direction transverse of the longitudinal axis of the member.

29 Claims, 3 Drawing Sheets

U.S. PATENT DOCUMENTS

| | | |
|---|---|---|
| 6,338,739 B1 | 1/2002 | Datta et al. |
| 6,416,540 B1 * | 7/2002 | Mathur ................. 623/1.15 |
| 6,776,194 B2 * | 8/2004 | Houston et al. ............. 138/39 |
| 6,946,003 B1 * | 9/2005 | Wolowacz et al. ....... 623/23.72 |
| 7,185,677 B2 * | 3/2007 | Houston et al. ............. 138/39 |
| 2003/0120257 A1 * | 6/2003 | Houston et al. ............ 604/523 |
| 2003/0225453 A1 | 12/2003 | Murch |

FOREIGN PATENT DOCUMENTS

| | | |
|---|---|---|
| EP | 1127557 A1 | 8/2001 |
| EP | 1254645 A1 * | 11/2002 |
| EP | 1314406 A2 | 5/2003 |
| FR | 2523361 | 9/1983 |
| FR | 8204332 | 9/1983 |
| FR | 2657945 A * | 8/1991 |
| FR | 2657945 A3 | 8/1991 |
| GB | 862795 | 3/1961 |
| GB | 933172 | 8/1963 |
| SU | 1697787 A1 | 12/1991 |
| WO | 9012550 A1 | 11/1990 |
| WO | 9823228 A1 | 6/1998 |
| WO | 9841168 A1 | 9/1998 |
| WO | 9955256 A1 | 11/1999 |
| WO | 0038591 A2 | 7/2000 |
| WO | WO 00/38591 | 7/2000 |
| WO | 0189419 A1 | 11/2001 |

* cited by examiner

INTERNAL FORMATION FOR A CONDUIT

FIELD OF INVENTION

The invention relates to an internal formation for a conduit and especially, a formation for modifying the flow of a fluid within a conduit.

BACKGROUND OF THE INVENTION

Vascular prosthesis, such as vascular grafts and stents, have been known for a number of years. Recently, it has been proposed that a helical formation formed on the internal surface of the vascular prosthesis can be used to generate desirable flow characteristics in blood flowing through the prosthesis, by encouraging spiral flow of the blood and so helping to reduce turbulence and/or dead spots with the fluid flow. It is believed that generating a spiral flow pattern in the blood, and thereby reducing turbulence and dead spots, can help to reduce vascular disease.

In this context, the term "spiral flow" refers to fluid flow in which there is a spiral and/or helical flow component to the fluid flow.

Examples of helical formations in vascular prosthesis are disclosed, for example, in International (PCT) Patent Application Nos. WO 00/38591 and WO 02/098325, and UK Patent Application No. 2369797 each of which is incorporated herein by reference.

However, one of the disadvantages of having a helical formation in a conduit is that the formation itself can create turbulence as the blood flows past the formation. This may have the unintentional effect of reducing or removing the spiral flow properties from the blood that the helical formation is intended to generate.

SUMMARY OF THE INVENTION

In accordance with a first aspect of the present invention, there is provided an internal formation for a conduit, the formation comprising a longitudinally extending member adapted to extend along an inside surface of at least a portion of the length of the conduit, the longitudinally extending member having an asymmetric profile in a direction transverse of the longitudinal axis of the member.

An advantage of providing a formation having an asymmetric profile is that it is possible to reduce the turbulent effects of the formation on a fluid flowing through the conduit.

Preferably, the longitudinally extending member extends helically along the length of the conduit, and preferably, extends helically along the internal side wall of the conduit.

Typically, a first surface of the longitudinally extending member is at least partially directed towards an inlet of the conduit and a second surface of the longitudinally extending member is at least partially directed towards the outlet of the conduit.

Preferably, the first surface intersects a diameter of the conduit at a smaller angle than the second surface intersects a diameter of the conduit. The first and second surfaces may be planar and/or curved. If one or both the surfaces are curved, they may be concave or convex, or a combination of concave and convex.

Typically, the angle that the first surface subtends with a diameter of the conduit extending through a portion of the profile closest to the centre of the conduit is less than 20°, preferably between 5° and 15°, and most preferably substantially 10°.

Typically, the first and second surfaces extend from the internal surface of the conduit towards each other and towards a central longitudinal axis of the conduit. The first and second surfaces are typically coupled together at an apex or by a third surface. Preferably, the third surface is a curved surface.

Preferably, the distance along the internal surface of the conduit from said diameter of the conduit to the point at which the second surface meets the internal surface of the conduit is substantially 0.25 of the internal width of the conduit.

In one example of the invention, the formation is for blood flow tubing, such as a vascular prosthesis. For example, a graft, a stent or a graft/stent combination. The formation may be in the form of an insert that is formed separately of the conduit and then mounted within the conduit, or may be integrally formed with the conduit, or may be formed by an elastic or non-elastic deformation of a side wall of the conduit. If the deformation is elastic, a former is retained around the conduit to maintain the internal formation.

Preferably, the formation is designed to effect spiral flow of a fluid, and typically a liquid, flowing through a conduit in which the insert is located. Where the conduit is blood flow tubing, the liquid is blood.

In accordance with a second aspect of the present invention, there is provided a conduit, the conduit including an internal formation in accordance with the first aspect of the invention.

The conduit may have one internal formation, or more than one internal formation. If there is more than one internal formation, the formations be in parallel around the conduit and/or in series along the conduit.

In addition, if there is more than one internal formation, the formations may be identical or may be different. If they are different, they may vary in height and/or the angle of the first and/or second faces.

BRIEF DESCRIPTION OF THE DRAWINGS

Examples of an internal formation in accordance with the invention will now be described with reference to the accompanying drawings, in which.

DETAILED DESCRIPTION

Figure 1:
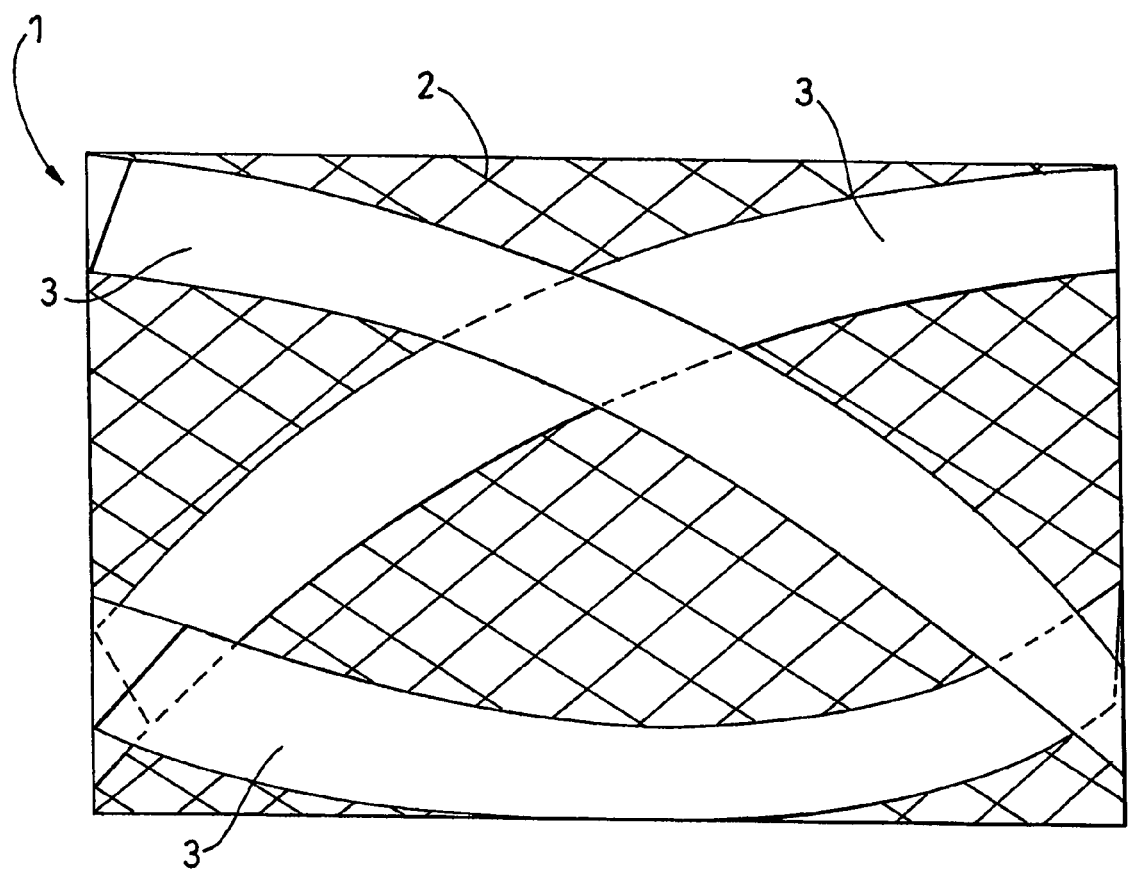
FIG. 1 is a schematic side view of a stent with the front half of the mesh body of the stent not shown for clarity.
Figure 2:
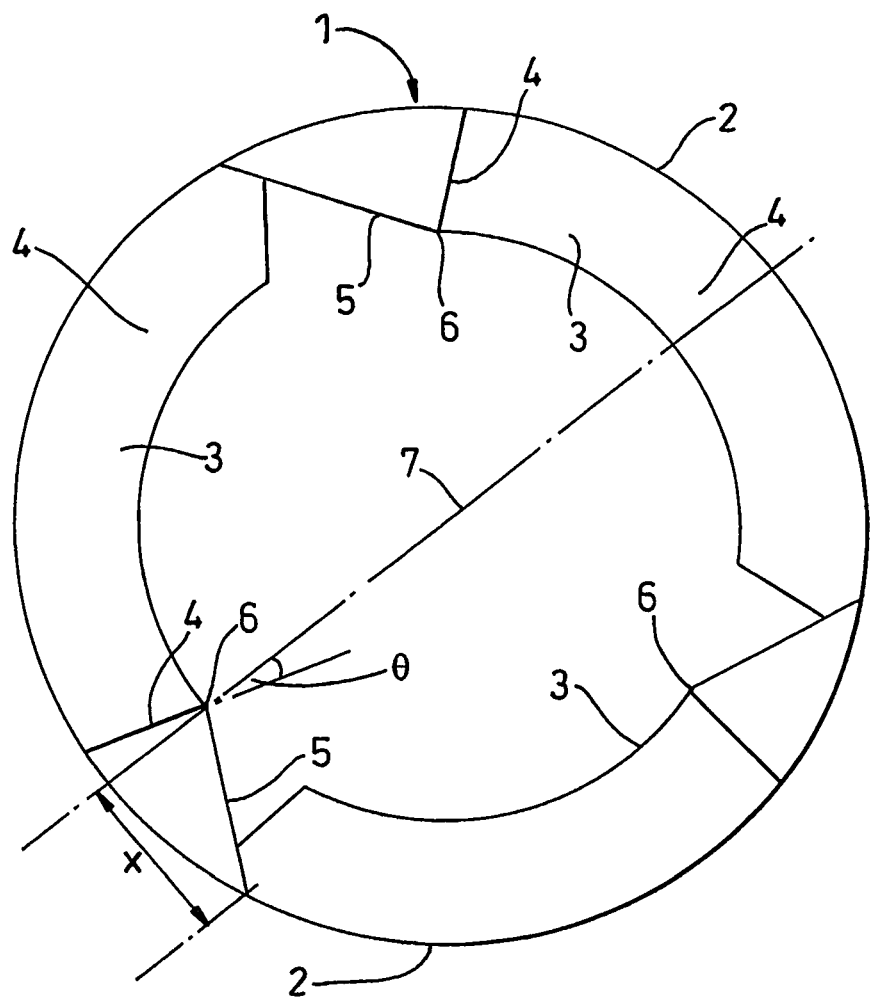
FIG. 2 is a cross-sectional view of the stent of FIG. 1 through a plane perpendicular to the longitudinal axis of the stent.

FIGS. 1 and 2 show a stent 1 having a cylindrical wire mesh body 2 and three internal formations in the form of inserts 3 mounted within the mesh body 2. The inserts 3 may be formed from a plastic material and may be mounted within the mesh body by being moulded onto the mesh body 2 so that the some of the mesh is entrapped within the inserts 3. The inserts 3 are spaced equidistantly around the inside of the mesh body 2 and are each in the shape of a helix so that the inserts 3 extend along and around the inside of the mesh body 2.

FIG. 2 is a cross-sectional view through the stent 1 in a plane perpendicular to the longitudinal axis of the stent 1, and looking in the direction of intended fluid flow through the stent 1. The stent 1 has a diameter of 3.5 mm and the height of each insert 3 is 0.5 mm. Each insert 3 has two faces, a first face 4 facing against the fluid flow direction and a second face 5 facing with the fluid flow direction. The first face 4 is steeper than the second face 5 and is at an angle θ of substantially 10° to a diameter 7 of the stent 1 intersecting apex 6 of the inserts 3. The angle of the second face 5 to the same diameter 7 is such that the distance x from the point at which the diameter intersects the internal surface of the mesh body 2 to the intersection of the second face 5 with the internal surface of the mesh body is approximately 0.25 of the internal diameter of the stent 1. Hence, the profile of the inserts 3 is asymmetric, with the first face 4 of the inserts 3 being steeper than the second face 5.

Figure 3:
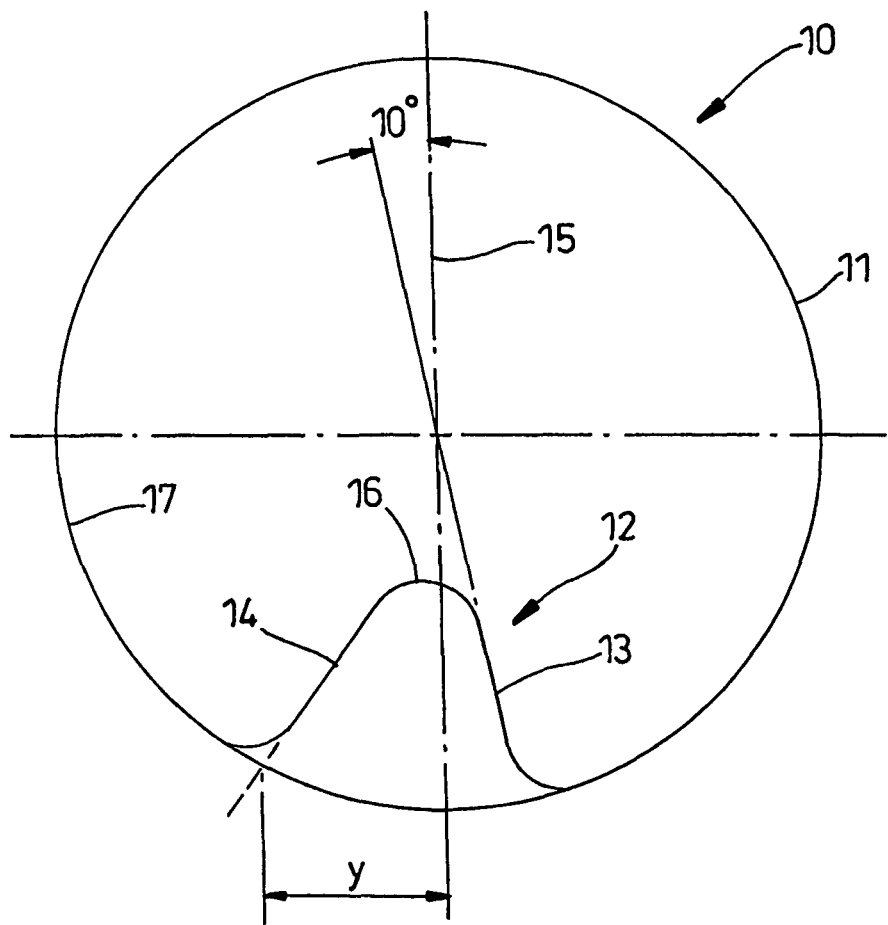
FIG. 3 is a cross-sectional view of a graft through a plane perpendicular to the longitudinal axis of the graft.

FIG. 3 shows a cross-sectional view of a graft 10 comprising a main body 11 having a deformation in the side wall of the body 11, the deformation being in the form of a helical formation 12. The helical formation 12 could be formed by any conventional means, such as described in UK Patent Application No. 2369797. Unlike the stent 1, the graft 10 only has a single helical formation 12. However, it is possible that the graft 10 could be provided with multiple helical formations 12.

The helical formation 12 has a first face 13 and a second face 14 coupled together by a curved surface 16. As shown in FIG. 3, the main, central section of the first face 13 is at angle of approximately 10° to a diameter 15 of the graft 10 that intersects the curved surface 16. The main, central section of the second face 14, if it is extrapolated down to the inside surface 17 of the graft 10, intersects the surface 17 at a distance y from where the diameter 15 intersects the surface 17. The distance y is approximately 0.25 of the internal diameter of the graft 10. For example, if the graft 10 has an internal diameter of 8 mm, the distance y is 2 mm.

In use, the graft is orientated so that the blood flow is against the first face 13.

The asymmetric profile of the inserts 3 and the helical formation 12 have the advantage of minimising turbulence in blood flow through the stent 1 and the graft 10 at typical blood flow rates and pressures. However, it is possible that similar or different asymmetric profiles could be used in certain blood flow applications, if desired or necessary.

Similar internal formations with asymmetric profiles could be used in other applications to reduce turbulence of fluid, and especially liquids, flowing within a conduit. However, for different fluid densities, flow rates and/or pressures, the angles of the first and/or second faces, and/or the height of the internal formation relative to the internal diameter of the conduit may be different.

The invention claimed is:

1. An internal formation for a conduit, the formation comprising a longitudinally extending member adapted to extend along an inside surface of at least a portion of the length of the conduit and projecting radially inwardly into the interior of the conduit, the longitudinally extending member having an asymmetric profile in a direction transverse of the longitudinal axis of the member, wherein a first surface of the longitudinally extending member is at least partially directed towards an inlet of the conduit and a second surface of the longitudinally extending member is at least partially directed towards an outlet of the conduit and wherein, at each radial cross-section of the conduit along which the longitudinally extending member extends, the angle that the first surface subtends with a diameter of the conduit extending through a portion of the profile of the longitudinally extending member closest to the radial centre of the conduit is less than 20°, and wherein the internal formation effects spiral flow of a fluid flowing through the conduit wherein, at each radial cross-section of the conduit along which the longitudinally extending member extends, the first surface subtends with the diameter of the conduit extending through the portion of the profile of the longitudinally extending member closest to the radial centre of the conduit at a smaller angle than the second surface subtends with the diameter of the conduit.

2. The internal formation according to claim 1, wherein the longitudinally extending member extends helically along the length of the conduit.

3. The internal formation according to claim 1, wherein the longitudinally extending member extends helically along the internal side wall of the conduit.

4. The internal formation according to claim 1, wherein the first surface comprises a planar portion and/or a curved portion.

5. The internal formation according to claim 4, wherein if the first surface comprises a curved portion, the curved portion is concave or convex, or a combination of concave and convex.

6. The internal formation according to claim 1, wherein the second surface comprises a planar portion and/or a curved portion.

7. The internal formation according to claim 6, wherein if the second surface comprises a curved portion, the curved portion is concave or convex, or a combination of concave and convex.

8. The internal formation according to claim 1, wherein the angle that the first surface subtends with the diameter of the conduit is between 5° and 15°, at each radial cross-section of the conduit along which the longitudinally extending member extends.

9. The internal formation according to claim 1, wherein the angle that the first surface subtends with the diameter of the conduit is substantially 10°, at each radial cross-section of the conduit along which the longitudinally extending member extends.

10. The internal formation according to claim 1, wherein the distance along the internal surface of the conduit from the point at which the diameter of the conduit intersects the internal surface of the conduit to the point at which the second surface meets the internal surface of the conduit is substantially 25% of the internal width of the conduit.

11. The internal formation according to claim 1, wherein the first and second surfaces extend from the internal surface of the conduit towards each other and towards a central longitudinal axis of the conduit.

12. The internal formation according to claim 11, wherein the first and second surfaces are coupled together at an apex or by a third surface.

13. The internal formation according to claim 12, wherein the third surface is a curved surface.

14. A conduit comprising an internal formation in accordance with claim 1.

15. The conduit according to claim 14, wherein the conduit is blood flow tubing.

16. The conduit according to claim 15, wherein the blood flow tubing is a vascular prosthesis.

17. The conduit according to claim 16, wherein the vascular prosthesis is a graft.

18. The conduit according to claim 16, wherein the vascular prosthesis is a stent.

19. The conduit according to claim 16, wherein the vascular prosthesis is a graft/stent combination.

20. The conduit according to claim 14, wherein the fluid is a liquid.

21. The conduit according to claim 14, wherein the conduit has two or more internal formations in accordance with claim 1.

22. The conduit according to claim 21, wherein the formations are in parallel around the conduit.

23. The conduit according to claim 21, wherein the formations are in series along the conduit.

24. The conduit according to claim 21, wherein the formations differ in height.

25. The conduit according to claim 21, wherein the formations differ in the angle of the first surfaces.

26. The conduit according to claim 21, wherein the formations differ in the angle of the second surfaces.

27. The internal formation according to claim 1 wherein the profile of the longitudinally extending member is uniform along the length of the longitudinally extending member.

28. The conduit according to claim 1, wherein the conduit is formed from one of a thermoplastic and thermosetting plastic.

29. The internal formation for a conduit, the formation comprising a longitudinally extending member adapted to extend along an inside surface of at least a portion of the length of the conduit and projecting radially inwardly into the interior of the conduit, the longitudinally extending member having an asymmetric profile in a direction transverse of the longitudinal axis of the member, wherein a first surface of the longitudinally extending member is at least partially directed towards an inlet of the conduit and a second surface of the longitudinally extending member is at least partially directed towards an outlet of the conduit, and wherein the first and second surfaces extend from the inside surface of the conduit towards each other and are coupled together at an apex or by a curved third surface, and wherein, at each radial cross-section of the conduit along which the longitudinally extending member extends the angle that the first surface subtends with a diameter of the conduit extending through a portion of the profile of the longitudinally extending member closest to the radial centre of the conduit is less than 20°, and wherein the internal formation effects spiral flow of a fluid flowing through the conduit wherein, at each radial cross-section of the conduit along which the longitudinally extending member extends, the first surface subtends with the diameter of the conduit extending through the portion of the profile of the longitudinally extending member closest to the radial centre of the conduit at a smaller angle than the second surface subtends with the diameter of the conduit.

* * * * *

UNITED STATES PATENT AND TRADEMARK OFFICE
CERTIFICATE OF CORRECTION

PATENT NO.         : 8,454,675 B2                                                                 Page 1 of 1
APPLICATION NO. : 10/562471
DATED              : June 4, 2013
INVENTOR(S)        : Houston et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 639 days.

Signed and Sealed this
Eighth Day of September, 2015

Michelle K. Lee
*Director of the United States Patent and Trademark Office*